(12) United States Patent
Ballevre et al.

(10) Patent No.: US 6,355,612 B1
(45) Date of Patent: Mar. 12, 2002

(54) PROTEIN MATERIAL FOR SLOW DIGESTION AND ITS USE

(75) Inventors: Olivier Ballevre, Lausanne; Clara L. Garcia-Rodenas, Forel; Kristel Reiffers-Magnani, La Tour-de-Peilz, all of (CH); Bernard Beaufrere, Chamaileres; Martial Dangin, Clermont-Ferrand, both of (FR); Francois Couzy, Savigny (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/807,554

(22) PCT Filed: Oct. 14, 1999

(86) PCT No.: PCT/EP99/07909

§ 371 Date: Jul. 9, 2001

§ 102(e) Date: Jul. 9, 2001

(87) PCT Pub. No.: WO00/22937

PCT Pub. Date: Apr. 27, 2000

(30) Foreign Application Priority Data

Oct. 16, 1998 (EP) .............................................. 98203452

(51) Int. Cl.[7] ........................ A61K 38/00; A61K 38/16; A23J 1/20; C07K 1/00; C07K 5/00

(52) U.S. Cl. .................................. 514/8; 514/2; 514/12; 530/350; 530/345; 530/360; 530/365; 424/439

(58) Field of Search ............................. 514/2, 8, 12, 23; 530/350, 324, 345, 360, 365; 424/185.1, 439

(56) References Cited

FOREIGN PATENT DOCUMENTS

| | | |
|---|---|---|
| EP | 0 799 577 A1 | 10/1997 |
| WO | 97/05785 | 2/1997 |

OTHER PUBLICATIONS

Boirie, Y. et al., "Slow and Fast Dietary Proteins Differently Modulate Postprandial Protein Accretion", Proc. Natl. Acad. Sci., vol. 94, pp. 14930–14935, Dec. 1997.

*Primary Examiner*—Avis M. Davenport
(74) *Attorney, Agent, or Firm*—Bell, Boyd & Lloyd, LLC

(57) ABSTRACT

The subject of the invention is the use of a protein material whose rate of digestion has been reduced, for the preparation of an enteral composition which makes it possible to modulate the postprandial plasma amino acid level, said protein material having been previously treated so as to convert the fast-digesting proteins which it contains to slow-digesting proteins, characterized in that the slow-digesting protein material is a material containing microparticulate gelled proteins combined with polysaccharides under conditions of thermodynamic incompatibility.

33 Claims, 3 Drawing Sheets

Figure 4:
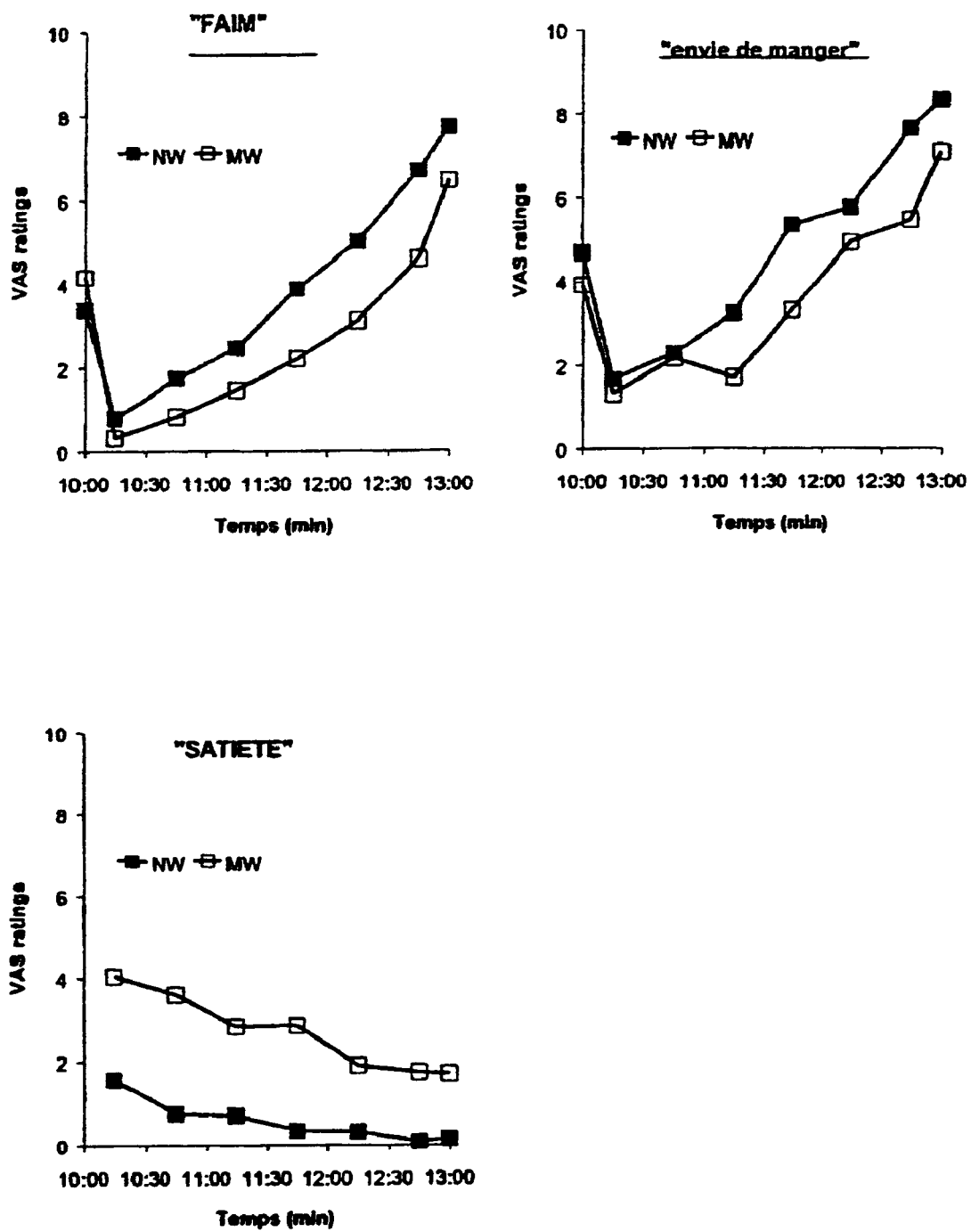

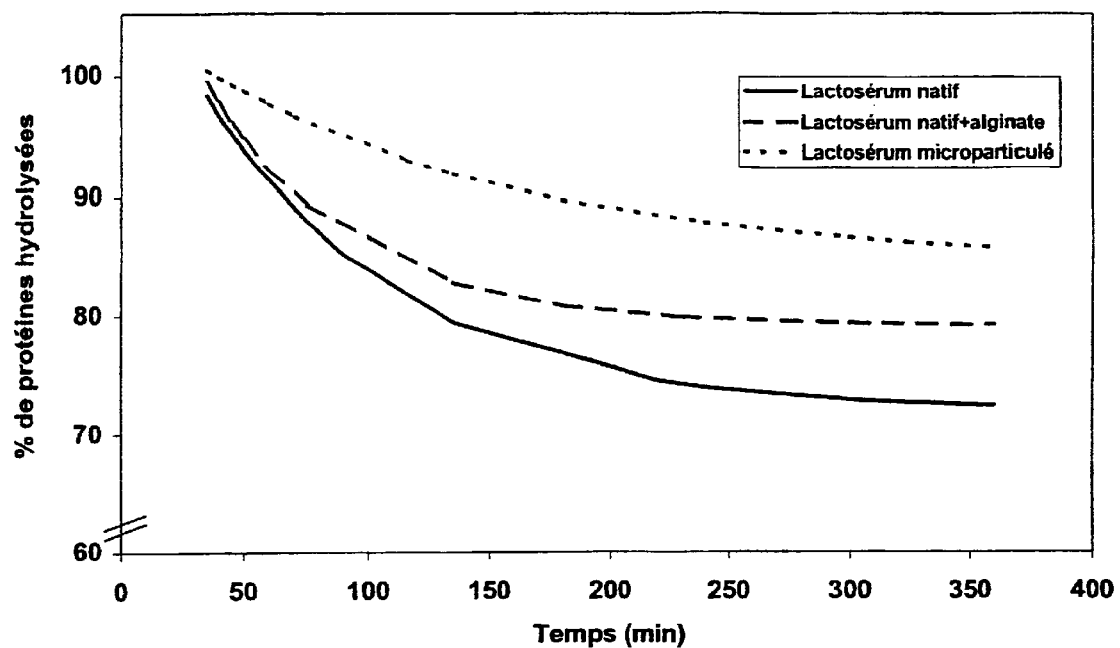
FIGURE 1: DIGESTION IN VITRO
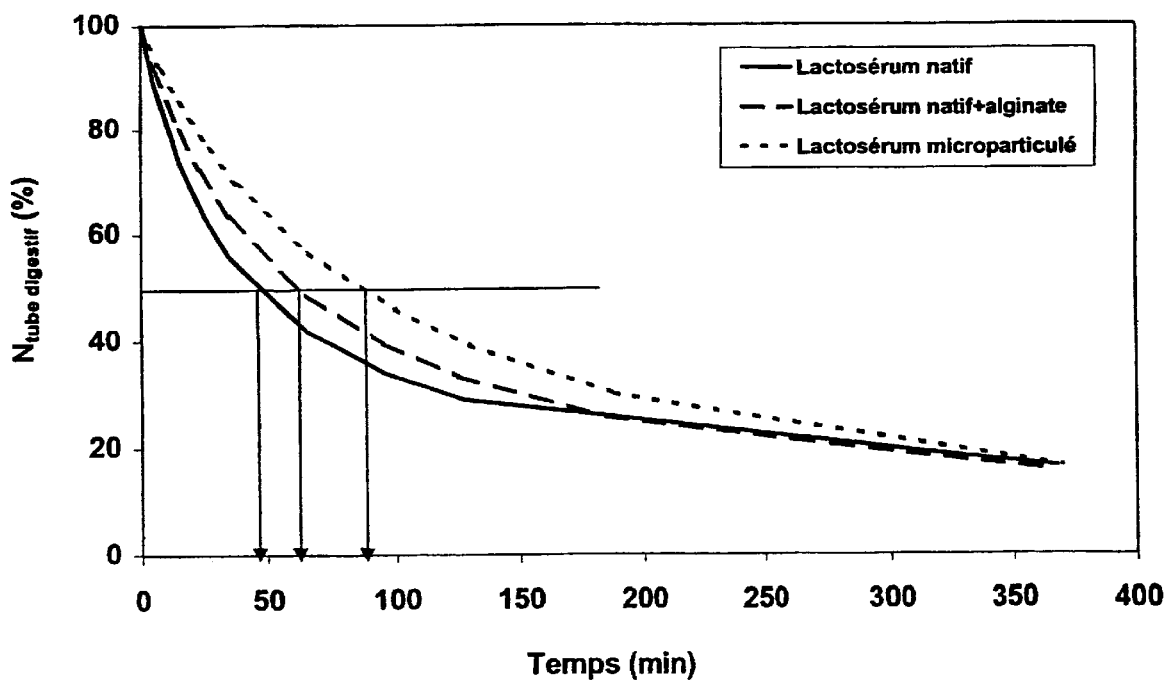
FIGURE 2: DIGESTION IN VIVO

FIGURE 3 : DIGESTION IN VIVO D'UN REPAS COMPLET
(lactosérum natif ( ■ ) et modifié ( ● )).
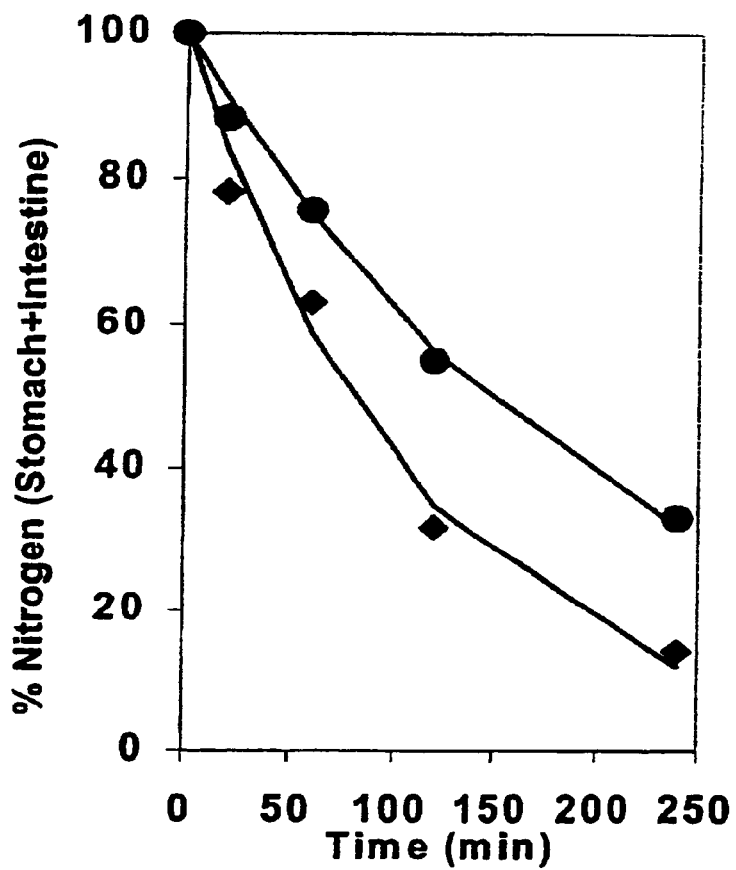

US 6,355,612 B1

PROTEIN MATERIAL FOR SLOW DIGESTION AND ITS USE

This application is a 371 of PCT/EP99/07909 filed Oct. 14, 1999.

BACKGROUND OF THE INVENTION

The subject of the invention is the use of protein material whose rate of digestion has been reduced, for the preparation of a composition which makes it possible to modulate the postprandial plasma amino acid level. The subject of the invention is also a composition intended to be administered by the enteral route to a mammal containing a protein material whose rate of digestion has been slowed down.

Because of a constant need for nutrients and the periodic nature of the diet in humans, the body has had to develop processes for storing the nutrients consumed in excess during meals and mechanisms for mobilizing these reserves during the period of physiological starving. The alternation of periods of food consumption and of starving are responsible for profound modifications in the various pathways for the metabolism of nutrients.

These nychthemeral variations affect the synthesis and the degradation of proteins and consequently the protein balance. Thus, the negative protein balance during the period of physiological starving becomes positive during the postprandial period, a phase for assimilating nutrients from the digestive tract. The relative importance of each phase then determines the variation in the body protein mass. It is therefore essential to be able to improve the postprandial protein gain in order to optimize the variation in the protein mass.

The ingestion of meals consisting of proteins causes an increase in the plasma amino acid level. This rise in the availability of amino acids is associated with a rearrangement of the various components of protein metabolism (protein degradation, protein synthesis, amino acid oxidation). Recently, Boirie et al. (*Proc. Natl. Acad. Sci. USA*, 94, 14930–14935, 1997) have shown in young healthy volunteers that the postprandial protein gain depended on the rate of digestion of the ingested proteins (period between ingestion and absorption of the nutrients by the body).

Some proteins with a fast rate of digestion, such as whey proteins, can have a high nutritive value, that is to say an adequate and balanced supply of amino acids which are essential for the human body, such as valine, leucine, isoleucine, phenylalanine, lysine, methionine, tryptophan and threonine. However, in spite of this good amino acid balance, the body's use of the amino acids derived from these proteins is not optimum, since they are digested too rapidly. Also, document WO 97/05785 describes a composition used in foods for newborns which contains slow-digesting proteins, said proteins having been modified beforehand so as to slow down the rate of digestion.

Other sources can therefore be used which contain proteins having a naturally slower rate of digestion, such as caseins, for example, but whose amino acids supply and balance are not optimum.

The present invention aims to provide for the nutritional needs of certain categories of people by means of proteins whose rate of digestion is reduced.

SUMMARY OF THE INVENTION

The invention thus relates to the use of a slow-digesting protein material for the preparation of a composition intended to be administered enterally to a mammal so as to modulate the postprandial plasma amino acid level, said protein material having been previously treated so as to convert the fast-digesting proteins which it contains to slow-digesting proteins, characterized in that the slow-digesting protein material is a material containing microparticulate gelled proteins combined with polysaccharides under conditions of thermodynamic incompatibility.

To date, it has never been proposed to reduce the rate of digestion of a protein with the aim of modulating the postprandial plasma amino acid level so as to: a) increase the postprandial protein gain; and/or b) avoid a metabolic overloading of certain organs and/or certain enzymes, and/or c) limit daily food intake by virtue of a satiating effect of these proteins, and/or d) compensate for certain dysfunctions in the metabolism of amino acids and more specifically for enzymatic deficiencies, e) improve the regeneration of tissues, in particular the processes of wound healing.

This treatment is particularly advantageous for proteins of high nutritional value which are digested too rapidly, this being so as to optimize the protein gain.

The subject of the invention is also a composition intended to be administered enterally to a mammal, containing a slow-digesting protein material which has been treated beforehand so as to convert the fast-digesting proteins which it contained to slow-digesting proteins, characterized in that the slow-digesting protein material is a material containing microparticulate gelled proteins combined with polysaccharides under conditions of thermodynamic incompatibility.

The compositions thus obtained may be particularly suitable for: minimizing the losses of body proteins in elderly persons, patients who are seriouly ill and people on a low-calorie diet; patients suffering from renal or hepatic disorders; patients suffering from disfunctions in the metabolism of amino acids such as, for example, hyperphenylalaninemia or other aminoacidopathies; patients treated with L-DOPA; and premature babies.

They may also be intended for the nutrition of pets, in particular that of elderly subjects, the young during the period of growth and for controlling the body weight of some subjects.

DETAILED DESCRIPTION OF THE INVENTION

In the context of the present invention, a slow-digesting protein material is a material which, when provided in the form of a solution and digested by 140–200 g rats, leads to a disappearance of half of the ingested nitrogen present in the digestive tract in more than 80 min.

Fast protein refers to proteins which, when they are ingested in the form of a solution by 140–200 g rats, leads to a disappearance of half of the ingested nitrogen present in the digestive tract in less than 70 min.

To carry out the present invention, a protein material, that is to say any material comprising proteins, whether they are of animal, plant or microbial origin, in particular proteins of milk, oil-producing plants, leguminous plants, egg or brewery yeasts, for example is used.

The materials containing proteins having a high nutritive value, based on the recommended intakes, are particularly indicated in the context of the present invention. These proteins may contain a balanced and high content of each of the amino acids essential for the body, such as lysine, tryptophan, leucine, isoleucine, valine, phenylalanine, methionine and threonine, for example.

Preferably, the protein-containing material (untreated) comprises fast-digesting proteins, such as for example whey proteins.

The protein-containing material is treated so that the rate of digestion of said proteins is slowed down. To this effect, the protein-containing material is mixed with polysaccharides and, under conditions of thermodynamic incompatibility, form microparticles which are gelled by heat treatment.

Indeed, biopolymers such as proteins and polysaccharides may exhibit thermodynamic incompatibility; that is to say that above a threshold concentration, they do not form a homogeneous mixture and separate spontaneously into two phases. One is enriched in proteins, the other is enriched in polysaccharides. At this initial stage, the separation of the two phases is achieved by formation of microscopic droplets, which may be gelled; in the case of protein droplets, a heat treatment often makes it possible to form a gel. Thus, the protein microparticle formation results from a phase separation and a spontaneous gelling of an aqueous mixture of proteins and polysaccharides (Syrbe, PhD Thesis, Techn. Univ. Munich, 1997).

The polysaccharides according to the present invention may be chosen in particular from alginates, xanthan gum, gum arabic, guar, starch, maltodextrins and dextrins, pectins, kappa-carrageenans, iota-carrageenans, lambda-carrageenans, methyl cellulose and carboxymethyl cellulose, sulfated dextrans and/or gellan gum.

The concentration of proteins and polysaccharides in the mixture may be respectively between 3 and 12% and between 0.2 and 1%. The protein/polysaccharide ratio may thus vary from 3:1 to 24:1.

The microparticles may for example be prepared from a mixture of a solution of alginate and a solution of serum proteins. The solution of alginate is preferably at 3% and pH 7 and the solution of serum proteins at 15%, pH 6.6. The mixture may thus be heated at a temperature of between 70 and 130° C. for a period of 1–60 minutes.

The microparticles obtained have a diameter preferably of between 200 nm and 100 microns.

The conditions for treating the protein-containing material must be preferably chosen so as to achieve a level of slowing down of the rate of digestion of said proteins such that when the treated protein material is orally administered in the form of a solution to 140–200 g rats, it leads to a disappearance of half of the ingested nitrogen present in the digestive tract in more than 80 min, for example.

The protein material thus treated may be advantageously used for the preparation of a food or pharmaceutical composition intended to be orally administered to a mammal so as to: 1) increase the postprandial protein gain, and/or 2) avoid a metabolic overloading of certain organs and/or certain enzymes, and/or 3) limit daily food intake by virtue of a satiating effect of these proteins, and/or 4) compensate for certain dysfunctions in the metabolism of amino acids and more specifically for enzymatic deficiencies, and/or 5) improve the efficacy of treatments with L-DOPA, 6) improve the regeneration of tissues, in particular the processes of wound healing.

The present use is however not limited to a protein material treated as described above. Indeed, other treatments may also induce a reduction in the rate of digestion of a protein-containing material. The present use is therefore intended to also use any protein material which has been treated beforehand so as to convert the fast-digesting proteins which it contained to slow-digesting proteins.

Thus, certain technological modifications, such as the thermal gelling, the mixing of these proteins with polysaccharides which can gel in the stomach, the formation of gelled microparticles as well as the preliminary supply of casomorphines in the form of a casein hydrolysate can make the rate of digestion of proteins slower.

It is possible, for example, to use one of the materials containing proteins which is cited above, combined with anionic polysaccharides.

The slow-digesting protein material is capable of improving or preventing problems linked with various physiological or physiopathological states. Indeed, the protein materials with a slow rate of digestion can act according to 4 principal modalities: by optimizing the postprandial protein gain, by avoiding excessive functioning for key organs or for certain enzymes, by optimizing treatments with L-DOPA and by increasing the sensation of satiety. The conditions governing the use of these proteins will depend in particular on the categories of people concerned.

In the context of the optimization of the postprandial protein gain, cases of undernourishment may be treated. Undernourishment frequently exists in elderly subjects or during diseases which comprise a substantial loss of body proteins—renal insufficiency, severe burns, trauma, surgical or infectious stress, inflammation, cancer or AIDS. This metabolic state manifests itself by a negative nitrogen balance which is the consequence of a fusion of the body, and more particularly muscle, proteins. Indeed, the muscle proteins are degraded so as to provide energy to the body and allow the redistribution of the amino acids to the synthesis of specific proteins.

In cases of undernourishment, the ingestion of slow-digesting protein material is capable of limiting this protein loss, by optimizing the postprandial protein gain. This protein material ought to increase the rate of physiological recovery, resistance to attacks, the quality of life and therefore the vital prognosis.

Renal abnormality, in the broad sense of the term, is an example of the use of the slow-digesting protein material which is not solely based on the optimization of the postprandial protein gain, although it is an essential component thereof. Indeed, during renal abnormalities, patients are subjected to a strict hypoprotein diet so as to reduce the production of nitrogenous waste. It is commonly accepted that such a diet has a favorable effect on the general condition, the quality of life and even on the renal function. However, this diet is very poorly tolerated by patients. The ingestion of slow-digesting protein material contributes toward:

1) reducing the production of nitrogen which should be subsequently eliminated by the kidneys;

2) distributing this production over a much longer period; and 3) increasing the satiating action of this type of protein in order to ensure better tolerance of the diet. Proteins with a slow rate of digestion are consequently particularly suitable for the nutrition of patients with renal disorders.

Likewise, the slow-digesting protein material may be prescribed for patients with pathological hepatic conditions. After a meal composed of various nitrogenous compounds (proteins, peptides, amino acids), the liver will try to maintain the amino acid concentration within physiological limits by breaking down a portion of the amino acids derived from the diet. A moderate arrival of dietary amino acids is capable of reducing the excessive activity of an organ which exhibits pathological conditions and which will consequently make it possible to avoid excessive work. In addition, the slow-digesting protein material induces a better postprandial protein gain.

During a deficiency in proteolytic pancreatic enzymes, the ingestion of slow-digesting protein material can contribute toward improving the digestion process. This benefit is brought about by the reduction in the quantity of substrate to be hydrolyzed by the proteolytic enzymes of the pancreas and therefore by the obtaining of a better enzyme/substrate ratio. Furthermore, with the slow-digesting protein material, there is a better postprandial protein gain.

In diseases where dysfunctions exist in the metabolism of amino acids and more specifically enzyme deficiencies in the pathway of degradation of these amino acids (phenylalaninemia and phenylketonuria, hypertyrosinemia, histidinemia, homocystinuria, amino acidopathies linked to branched amino acids, for example), the accumulation of these amino acids or of one of their degradation products produces neurological and clinical complications. To avoid this accumulation, a dietetic treatment is prescribed. It consists of a diet which does not contain—or contains a very small quantity of—the amino acid implicated in the development of the disease. The specific products developed for these populations are composed either of free amino acids, or of highly hydrolyzed proteins. However, these mixtures do not possess a pleasant taste. Furthermore, to avoid diarrhea following on from the hyperosmolarity of the products, consumers should ingest the products in the form of small meals. The protein material which possesses both a slow rate of digestion and a small content of the implicated amino acid, makes it possible to improve the taste and therefore the tolerance of the diet, to limit the risk of diarrhea, to avoid plasma fluctuations in amino acids, and to increase the postprandial protein gain.

The use of slow-digesting protein material can also be envisaged for people who are not undernourished, such as premature babies, newborns, children, obese individuals and elderly persons, for example.

The ingestion of slow-digesting protein material, in premature babies, newborns or children who are not undernourished, by providing a better yield of use of the dietary proteins, is capable of promoting body growth.

The slow-digesting protein material, by reducing the food intake by a satiating mechanism, may be administered to people with disorders of weight homeostatis (obesity) or during episodes of bulimia. It can limit the reduction in the protein mass subsequent to being on a low-caloric diet. These two combined factors make it possible to reduce their fatty mass with, on the one hand, greater ease for reducing their supplies and, on the other hand, a better preservation of their protein mass.

In elderly persons, compared with young subjects, there is a reduction in the body protein mass, a reduction which has an influence on the autonomy, the resistance to attacks (diseases, various stresses) and the ability to recover from these attacks. Furthermore, aging is associated with a reduction in renal activity. The slow-digesting protein material, by therefore allowing better preservation of the protein mass, thus makes it possible to avoid renal excesses.

The protein material with a slowed rate of digestion, by providing the amino acids in a more continuous and regular manner, makes it possible to promote the synthesis of novel tissue materials which are involved in the processes of wound healing or of regeneration of biological tissues.

The protein material with a slowed rate of digestion may be intended for the nutrition of pets, in particular that of elderly subjects and the young in the growth phase. It can also be administered to certain subjects so as to control their body weight.

The proteins contained in the compositions according to the invention can provide from 5 to 100% of the total energy, in particular from 8 to 30%, and preferably from 10 to 20%. In the case of the compositions intended for use as pet food, the protein content may be up to 40% on the basis of the dry extract.

These compositions preferably comprise a source of carbohydrates providing 0 to 70% of the total energy. The carbohydrates are important nutrients for re-establishing the energy balance. All carbohydrates can be used, in particular maltodextrins, sucrose, lactose and glucose, for example.

The compositions may comprise a source of lipids which provide up to 35% of the total energy. Vegetable oils are recommended, in particular those of soybean, oil palm, coconut, sunflower and the like. In the case of the compositions intended for use as pet food, the source of lipids can provide up to 60% of the total energy.

The energy value of these compositions may be between 70 and 200 Kcal/100 ml, for example.

In the case of the compositions intended for infant nutrition, the proteins preferably represent 0.45 to 0.7 g/100 kJ, the carbohydrates preferably 1.7–3.4 g/100 kJ and the lipids preferably 0.1–1.5 g/100 kJ.

In the case of compositions intended for patients suffering from phenylketonurea, the protein material may contain about 50% of caseinoglycomacropeptides, a source of carbohydrates, a source of lipids and vitamins and minerals.

The compositions according to the present invention may be prepared in all sorts of ways, the steps of manufacture generally including a dispersion of the ingredients in water, emulsification and pasteurization.

The compositions may be prepared in the form of liquid or semisolid concentrates or drinks or in the form of a powder which may be reconstituted in water, for example. They may also be provided in a solid form, such as cereals, nutritional bars, for example.

Minerals, vitamins, salts, emulsifiers or flavoring compounds may also be added to the compositions, as required. The vitamins and minerals may represent from 25 to 250% of the recommended daily supplies. In the case of infant formulas, the quantities of vitamins and minerals prescribed by the European Directive are added.

The present invention is described in greater detail below with the aid of the examples which are given by way of illustration of the subject of the invention and do not constitute in any manner a limitation thereto. The percentages are given by weight unless otherwise stated. These examples are preceded by a brief description of the figures.

FIG. 1: presents the percentage of proteins hydrolyzed as a function of time for the in vitro digestion of native whey, native whey+alginate and microparticulate whey+alginate.

FIG. 2: represents the percentage of nitrogen ingested and remaining in the digestive tract (stomach+small intestine) as a function of time during the digestion in vivo of solutions of native whey, native whey+alginate or microparticulate whey+alginate.

FIG. 3: represents the percentage of nitrogen ingested and remaining in the digestive tract (stomach+small intestine) as a function of time during the digestion in vivo of complete meals containing proteins of native whey ( ) or of modified whey+alginate (•).

FIG. 4: represents the curves for "hunger", "desire to eat" and "distension of the stomach" for meals based on proteins of native whey (NW) and modified whey (MW) as a function of time.

EXAMPLE 1

Kinetics of Digestion of Protein Solutions

The microparticles of whey are prepared from a mixture of 3% alginate solution (Manucol DM, Kelco) at pH 7 and a 15% solution of serum proteins (Lacprodan DI-9223; Danmark Protein) whose pH is 6.6.

The concentrations in the mixture are 1% of alginate and 10% of proteins. The mixture is heated at 80° C. for 10 minutes and will be diluted two-fold so as to obtain a final protein concentration of 5%. The microparticles have a diameter between 500 nm and 5 microns.

The enzymatic hydrolysis in vitro and in vivo of the microparticles is compared with that of a 5% solution of native proteins and with that of a mixture of native proteins (5%) and of alginate (0.5%).

The enzymatic digestion in vitro is carried out according to the method described by Savalle et al. (*J. Agric. Food Chem.*, 37, 1336, 1989) and modified in the following manner: the samples, containing 250 mg of proteins, are incubated at 37° C. in the presence of pepsin (1 mg) at pH 1.9 for 30 minutes. The medium is then neutralized at pH 7.5 with sodium hydroxide and digestion with pancreatin is carried out for 5 h 30 min. The degree of hydrolysis is determined by measuring the free amino groups by the TNBS method (Adler-Nissen, *J. Agric. Food Chem*, 27, 1256, 1979). Before incubation, the samples were ground by passing through a syringe 1 mm in diameter so as to simulate in vitro the conditions of gavage which are used in vivo in rats.

The kinetics of hydrolysis in vitro is represented in FIG. 1. The results show that the microparticulate whey is digested more slowly than the native whey containing alginate or not, this being more particularly during the first two hours of hydrolysis.

In vitro, the native whey is only about 30% hydrolyzed (the value 100% of proteins not hydrolyzed plotted on the graph corresponds to the quantity of $NH_2$ groups contained in the whey, according to Adler-Nissen).

For the study of digestion in vivo, 21 male Sprague-Dawley rats (Iffa-Credo, F-6210 L'Arbresle, France), weighing 160 to 180 g, are randomly distributed into 11 groups. After a period of acclimatization of at least 2 days, the animals are placed in metabolic cages (to avoid coprophagy) and starved for 22 hours. The rats are then fed by gavage with a suspension of 5 ml of test protein at 5%.

The rats are anesthetized at 0, 10, 20, 30, 60, 90, 120, 180, 240, 360 minutes after gavage. The abdominal cavity is opened and blood samples are taken from the portal vein and the dorsal aorta. The animals are then sacrificed; the stomach and the small intestine are separated from the abdominal cavity. The gastric and intestinal contents are recovered by washing the luminal content with a 0.9% NaCl solution.

The blood samples are mixed with heparin and centrifuged. The plasma samples are deproteinized with sulfosalicylic acid at 3.6% (w/v, final concentration) and then stored at −80° C. up to the analysis of the amino acids (amino acid analyzer, system 6300-Beckman).

The gastrointestinal contents are kept at low temperature and their total nitrogen content is rapidly analyzed.

The percentage of nitrogen ingested and remaining in the digestive tract (stomach+small intestine) as a function of time is represented in FIG. 2.

The results show that in solution, the microparticulate whey is digested less quickly than the native whey, and that this effect is due to the modification and not to the presence of alginate. The disappearance of half of the ingested nitrogen from the digestive tract occurs after 90 min for the microparticulate whey whereas it occurs after 45 minutes for the native whey.

EXAMPLE 2

Kinetics of Digestion of the Proteins Contained in Complete Meals

The procedure is carried out as described in Example 1, the difference being that the rats are force-fed with a complete meal of the following composition (% by weight): 5% of proteins of native or microparticulate whey, 8% of soybean oil, 0.1% of emulsifier, 17% of sucrose, 8% of maltodextrins and 61.9% of water.

The results presented in FIG. 3 indicate that in a complete meal, the protein whose rate of digestion has been slowed down is more slowly digested than the native protein. The disappearance of half of the ingested nitrogen from the digestive tract occurs after 145 minutes for the microparticulate whey whereas it occurs after 78 minutes for the native whey.

EXAMPLE 3

Study of Satiety in Human Volunteers

Materials and methods

Samples:

The isolate of whey proteins (NW) was provided by MD-Foods. The protein solutions for drinking were prepared by mixing the ingredients given in Table 1 in dimineralized water, and then left overnight at 4° C., with stirring.

The proteins of microparticulate whey (MW) were prepared from NW according to the following steps:

1) dissolve the alginate and the remainder of the ingredients separately in water.
2) Mix the 2 solutions so as to obtain the final composition given in Table 1, and distribute the composition into stainless steel dishes of 200 g each, sealed and then heated in an oven at a temperature of 105° C. until the internal temperature reaches 78° C., and then cooled.
3) The drinks and the gel of whey proteins are flavored, sweetened and colored to enhance their palatability. Flavorings of different sorts and at different concentrations were tested by a panel of 8 people and the products and doses most frequently chosen were used for the final compositions (Table 1).

The meals (400 g) have isoenergy levels (178 Kcal/portion) and isoprotein levels (40 g/portion).

TABLE 1

| Composition of the protein meals (in g per portion of 400 g) | | |
|---|---|---|
| | NW | MW |
| Isolate of whey proteins | 47.6 | 47.6 |
| Sodium alginate | | 2.0 |
| Artificial sweetener | 1.6 | 1.6 |
| Sucrose | 8.0 | 8.0 |
| Caramel flavor | 0.8 | 0.8 |
| Caramel coloring | 0.02 | 0.02 |
| Water | 342.0 | 340.0 |

Subjects 5 human volunteers having an average age of 32.5±6.9 and a mean body mass index of 22.3±1.7 $Kg/m^2$, received one of the 2 meals on each of the 2 days of the experiment.

Protocol

The subjects did not consume any alcoholic drinks on the day before the study and had a light dinner before 8 pm and fasted up to the beginning of the protocol. 3 meals were consumed on the day of the protocol:

1) A light and standard breakfast consisting of a slice of wholemeal bread, 5 g of butter, 10 g of jam and coffee or tea with milk (150 Kcal). It was served at 7.45 am and was consumed in 10–15 min.
2) The test meals were served at 10 am and consumed in about 15 minutes.
3) A meal based on pasta with tomato sauce and kiwis was served at 1 pm.

The volunteers noted their sensation of hunger, feeling hungry and distension of the stomach, on a visual analog scale (10 cm) at 30 minute intervals between 10 am and 1 pm.

During the 1 pm meal, where the volunteers ate until they were full, the quantity of pasta and tomato sauce ingested was checked and weighed. The quantity of kiwis consumed was checked per unit (100±5 g per unit). The subjects noted in a notebook the foods consumed during the rest of the day of the study. The quantity of the various foods consumed during lunch and the rest of the day made it possible to estimate the number of Kcal ingested, using the food composition table by McCance and Widdowson (1991).

Results

The curves for "hunger", "feeling hungry" and "distension of the stomach" are given in FIG. 4. The proteins of native whey (NW) and modified whey (MW) behave differently. The return of hunger and of the desire to eat is slower with the meal based on MW and the sensation of distension of the stomach lasts longer for MW.

The mean calorie supply during the meal and during the rest of the day was compared after a first load of NW and MW. The results in Table 2 show that in the case of MW, this supply is reduced.

The results show a more hunger-satisfying effect of modified whey compared with native whey.

TABLE 2

| Calorie supply in Kcal | | |
|---|---|---|
| | NW | MW |
| Meal | 1459 ± 772 | 1091 ± 333 |
| Rest of the day | 933 ± 273 | 731 ± 262 |
| Meal + rest of the day | 2392 ± 682 | 1822 ± 547 |

EXAMPLE 4

Study of the Nutritional Quality of the Modified Protein

Materials and methods

The proteins of microparticulate whey MW were prepared by mixing a solution of alginate at 2% by weight and 20% by weight of a solution of whey proteins in a 1:1 ratio. The composition is distributed into 200 ml dishes and then treated as described in Example 2.

Two diets are prepared by mixing, in a mixer, the ingredients presented in Table 3. They are given for 21 days to 2 batches of 10 male Sprague-Dawley rats weighing about 60 g at the beginning of the study. The variation in weight, as well as the quantity of diet food ingested during the 3 weeks are measured. In the second week of the study, the animals are transferred in metabolic cages and the feces and urine are collected for 7 days.

TABLE 3

| Composition of the diets | | |
|---|---|---|
| | NW diet | MW diet |
| Whey proteins | 5.972 | 5.972 |
| Vitamins | 0.500 | 0.500 |
| Minerals | 1.750 | 1.750 |
| Choline bitartr. | 0.100 | 0.100 |
| Cellulose | 2.500 | 2.500 |
| Soybean oil | 5.000 | 5.000 |
| Maltodextrin | 34.178 | 33.678 |
| Alginate | | 0.500 |
| Water | 50.000 | 50.000 |
| TOTAL | 100.000 | 100.000 |

NW: proteins of native whey, MW: proteins of modified whey

The following parameters were then measured:

digestibility (D), biological value (BV), net protein use (NPU), protein efficacy ratio (PER)

The results given in Table 4 show a slight decrease in the digestibility of nitrogen in the case of an MW diet, which has no effect on the net protein use (NPU) by virtue of a slightly improved absorbed nitrogen use (BV). The protein efficacy ratio is moreover not affected by the treatment (PER).

The results show that the protein microparticle formation does not adversely affect its nutritional quality.

TABLE 4

PER; digestibility, BV and NPU for rats fed with NW diet and MW diet for 21 days (mean ± 95% confidence interval).

| | PER | Digestibility | BV | NPU |
|---|---|---|---|---|
| NW | 3.38 ± 0.11 | 97.6 ± 0.3 | 68.7 ± 6.7 | 67.0 ± 4.7 |
| MW | 3.30 ± 0.18 | 95.6 ± 0.4 (*) | 73.1 ± 4.1 | 69.9 ± 2.8 |

(*) Significantly different from $p < 0.05$

EXAMPLE 5

Food Composition for Unweaned Babies

A food composition for unweaned babies is prepared in the form of a soluble powder having the composition defined in Table 5 below. This powder is used at the rate of 13% in water, which corresponds to an energy density of the order of 70 kcal/100 ml.

To prepare this powder, water is purified by reverse osmosis, it is heated to 70° C., a source of proteins and a source of carbohydrates are added to it, a source of lipids in which fat-soluble vitamins have been dispersed beforehand is added to it, the mixture is heated at 80° C. for 5 min by injection of steam, it is cooled to 60° C. and minerals and water-soluble vitamins are added to it, it is homogenized in 2 stages at 10 mPa and then at 7 mPa, it is spray-dried under a hot air stream to a water content of 4%, and then it is reduced to a fine powder which is soluble in water.

Vitamins and minerals are added to the composition in a quantity satisfying the recommended daily intakes.

TABLE 5

| PROTEINS | 2.3 g/100 Kcal |
|---|---|
| Casein | 40% |
| Whey treated according to Example 1 | 60% |
| CARBOHYDRATES | 10 g/100 Kcal |
| Lactose | 100% |
| LIPIDS | 5.5 g/100 Kcal |
| Milk fat | 70% |
| Canola oil | 15% |
| Corn oil | 14% |
| Soybean lecithin | 1% |

EXAMPLE 6

Enteral Composition

A liquid enteral composition containing the ingredients defined in Table 6 below is prepared in the same manner as in Example 5, the difference being that the mixture is homogenized at 150° C. by injection of steam, it is cooled to 75° C. and it is aseptically packaged in containers. Vitamins and minerals are added to it in a quantity satisfying the recommended daily intakes.

This composition has an energy density of 100 Kcal/100 ml.

TABLE 6

| PROTEINS | 6.5 g/100 ml |
|---|---|
| Whey treated according to Example 1 | 100% |
| CARBOHYDRATES | 11.3 g/100 ml |
| Solids of a corn syrup | 56% |
| Sucrose | 34.4% |
| Xanthan | 9.6% |
| LIPIDS | 3.4 g/100 ml |
| Coconut oil | 50% |
| Canola oil | 30% |
| Corn oil | 14% |
| Soybean lecithin | 6% |

EXAMPLE 7

Nutritional Supplement for Patients Suffering from Renal Insufficiency

A liquid composition intended for people suffering from renal insufficiency, containing the ingredients defined in Table 7 below, is prepared in the same manner as in Example 6. Vitamins and minerals are added in a quantity satisfying the recommended daily intakes.

This composition has an energy density of 200 Kcal/100 ml.

TABLE 7

| PROTEINS | 5 g/100 ml |
|---|---|
| Whey treated according to Example 1 | 100% |
| CARBOHYDRATES | 27 g/100 ml |
| Solids of a corn syrup | 56% |
| Maltodextrin | 34.4% |
| Sucrose | 9.6% |
| LIPIDS | 8 g/100 ml |
| Coconut oil | 50% |

TABLE 7-continued

| Canola oil | 30% |
|---|---|
| Corn oil | 14% |
| Soybean lecithin | 6% |

EXAMPLE 8

Food Composition for Patients Suffering from Phenylketonuria

A food composition for phenylketonurics is prepared in the same manner as in Example 5, in the form of a soluble powder and having the composition defined in Table 8 below. Vitamins and minerals are added in a quantity sufficient for the recommended daily intakes.

This powder is used at the rate of 15% in water, which corresponds to an energy density of the order of 70 kcal/100 ml and to a phenylalanine content of the order of 10 mg/100 ml.

TABLE 8

| PROTEINS | 3.3 g/100 Kcal |
|---|---|
| Caseinoglycomacropeptide treated according to Example 1 | 50% |
| Free amino acids<br>L-Arginine, L-Cystine, L-Glutamine, L-Glycine<br>L-Histidine, L-Isoleucine, L-Leucine,<br>L-Lysine, L-Methionine, L-Proline,<br>L-Tryptophan, L-Tyrosine, L-Valine | 50% |
| CARBOHYDRATES | 13 g/100 Kcal |
| Lactose | 100% |
| LIPIDS | 3.9 g/100 Kcal |
| Canola oil | 60% |
| Corn oil | 39% |
| Soybean lecithin | 1% |

EXAMPLE 9

Low-calorie Nutritional Supplement

A nutritional composition intended for people wishing to reduce or maintain their weight is prepared in the form of a soluble powder, flavored with chocolate and having the composition defined in Table 9 below. Vitamins and minerals are added in a quantity satisfying the recommended daily intakes.

This powder is used at the rate of 13% in skimmed milk, which corresponds to an energy density of the order of 100 kcal/100 ml.

To prepare this powder, all the ingredients are mixed in the dry state, the mixture is conditioned by wetting and drying again to a water content of 4%, then the mixture is reduced to a fine powder which is soluble in water.

TABLE 9

| PROTEINS | 35 g/100 g |
|---|---|
| Whey treated according to Example 1 | 100% |
| CARBOHYDRATES | 63 g/100 g |
| Sucrose | 65% |
| Maltodextrin | 10% |
| Cellulose | 25% |

EXAMPLE 10

Flavored Composition for Elderly Persons

A liquid nutritional composition, intended for elderly persons, flavored with strawberry and having the composition defined in Table 10 below, is prepared as described in Example 6. Vitamins and minerals are added in a quantity satisfying the recommended daily intakes.

TABLE 10

| INGREDIENTS | COMPOSITION (g/100 g) |
|---|---|
| Sucrose | 6.0750 |
| Maltodextrins | 4.8830 |
| Proteins | 7.5000 |
| Rapeseed oil | 1.3550 |
| Corn oil | 0.4670 |
| Corn starch | 0.4070 |
| Strawberry flavor | 0.1960 |
| Monoglycerides | 0.1830 |
| Vitamin C | 0.0324 |
| Dibasic Na phosphate | 0.0249 |
| Iota caraageenans | 0.0247 |
| Micronutrients | 0.0187 |
| Choline chloride | 0.0183 |
| Minerals: | 0.2704 |
| K, Fe, Zn, Mg | |
| Coloring | 0.0020 |
| Water | 78.566 |
| TOTAL | 100.0000 |
| Calories/g | 1.00 |

EXAMPLE 11

Composition for Use as Pet Food

Three variants of a highly palatable meat-based cat food are prepared to which premixes of minerals and vitamins, as well as taurine are added. The whole is gelled either by addition of guar gum at 0.3% (variant A), or by addition of xanthan gum at 0.5% (variant B). The guar gum and the xanthan gum are added after wetting. However, variant B containing xanthan gum is then finely ground by means of a rotary apparatus incorporating a grid. The third variant (variant C) is identical to variant A, but it is treated by finely grinding in the same manner as variant B containing xanthan gum. The variants are then packaged in boxes with a capacity of 156 g and then sterilized in industrial autoclaves. Although the palatability remains similar between the 3 variables, the xanthan gum contributes to a texture which is markedly different from that of the other variants.

The nutritional composition of the variants is indicated below:

| | Moisture (%) | Proteins (g/100 g) | Fat (g/100 g) | Fibers (%) | Ash (%) | Carbohydrates (%) |
|---|---|---|---|---|---|---|
| Vari-ant A | 79.4 | 12.9 | 5.2 | 0.14 | 1.65 | 0.65 |
| Vari-ant B | 79.8 | 12.5 | 5.3 | 0.10 | 1.41 | 0.82 |
| Vari-ant C | 79.4 | 12.8 | 5.1 | 0.11 | 1.88 | 0.70 |

A group of 36 adult cats consumed a food similar to the control diet for one week, and was then separated into 3 groups of 12 cats each consuming either variant A, variant B, or variant C, for 13 days. At the end of the 13 days, the treatments were switched for another 13 days. Thus, each cat received two variants, each for 13 days, according to an open block crossover experimental design.

At the end of the test, it was observed that some cats had soft feces. This was therefore taken into account in the interpretation of the results.

During the first phase of the study, it was observed that the cats receiving variable B lost more weight in a statistically significant manner at $p=0.05$ than for the other variants, in spite of similar food intakes. This effect was maintained when the results for the cats which had soft feces were excluded from the analysis, the difference in weight loss between variants A and B remaining statistically significant.

| | Food intake (g/day.cat) | Variation in weight (% of the initial weight) | |
|---|---|---|---|
| | | All cats | Soft feces excluded |
| Variant A | 41.1 ± 11.9 | −0.11 ± 2.76 | +0.03 ± 2.85 |
| Variant B | 41.7 ± 12.7 | −4.01 ± 2.52 | −3.22 ± 1.78 |
| Variant C | 43.4 ± 11.2 | −1.81 ± 2.56 | −1.88 ± 2.75 |

This result indeed shows the benefit of the present invention for controlling the body weight in pets.

EXAMPLE 12

Food for Puppies

A complete extruded food for puppies was prepared based on cereals and sources of proteins. Its nutritional composition is the following: proteins at least 22%, lipids at least 8%, fiber 4.5% approximately, moisture 12% at most, calcium at least 1%, phosphorus at least 0.8%. The addition of xanthan gum to the composition by appropriate means makes it possible to obtain beneficial effects on the growth of the puppies.

EXAMPLE 13

Extruded food as described in Example 12, in which the content of lipids is at least 5% but less than 8%. The addition of xanthan gum to the composition by appropriate means makes it possible to help to limit bodyweight gain in dogs.

What is claimed is:

1. A method for modulating the postprandial plasma amino acid levels in a mammal comprising the step of administering to a mammal a composition including a slow-digesting protein, the slow-digesting protein being a protein material containing microparticulate gelled proteins that are combined with polysaccharides under conditions of thermodynamic incompatibility, the protein material having been treated so as to convert any fast-digesting proteins which the protein material contains to slow-digesting proteins.

2. The method of claim 1 wherein the composition modulates the postprandial plasma amino acid levels by increasing a postprandial protein gain in the mammal.

3. The method of claim 1 wherein the composition modulates the postprandial plasma amino acid levels by avoiding a metabolic overloading of certain organs in the mammal.

4. The method of claim 1 wherein the composition modulates the postprandial plasma amino acid levels by avoiding a metabolic overload of certain enzymes in the mammal.

5. The method of claim 1 wherein the composition modulates the postprandial plasma amino acid levels by limiting daily food intake in the mammal by virtue of a satiating effect of these proteins.

6. The method of claim 1 wherein the composition modulates the postprandial plasma amino acid levels by compensating for certain dysfunctions in the metabolism of amino acids in the mammal.

7. The method of claim 1 wherein the composition modulates the postprandial plasma amino acid levels by improving the regeneration of tissues in the mammal.

8. The method of claim 1 wherein the mammal is a human suffering from renal insufficiency.

9. The method of claim 1 wherein the mammal is a human suffering from hepatic pathologies.

10. The method of claim 1 wherein the mammal is a human suffering from dysfunctions in the metabolism of at least certain amino acids.

11. The method of claim 1 wherein the mammal is a pet.

12. The method of claim 11 wherein the pet is elderly.

13. The method of claim 11 wherein the pet is in a period of growth.

14. The method of claim 1 wherein the protein material is gelled by heat treatment.

15. The method of claim 1 wherein the polysaccharides are chosen from the group consisting of: alginates; xanthan gum; gum arabic; guar; starch; maltodextrin and dextrins; pectins; kappa-carrageenans; iota-carrageenans; lambda-carrageenans; methyl cellulose and carboxymethyl cellulose; sulfated dextrans; and gellan gum.

16. A composition intended to be enterally administered to a mammal containing a slow-digesting protein material containing microparticulate gelled proteins combined with polysaccharides under conditions of thermodynamic incompatibility.

17. The composition of claim 16, wherein the polysaccharides are chosen from the group consisting of: alginates; xanthan gum; gum arabic; guar; starch; maltodextrin and dextrins; pectins; kappa-carrageenans; iota-carrageenans; lambda-carrageenans; methyl cellulose and carboxymethyl cellulose; sulfated dextrans; and gellan gum.

18. The composition of claim 16 wherein the proteins are gelled by heat treatment.

19. The composition of claim 16 comprising:
a source of proteins providing at least 8% of the total energy;
a source of carbohydrates providing up to 70% of the total energy; and
a source of lipids providing up to 35% of the total energy.

20. The composition of claim 16 having an energy density of between approximately 70 to about 200 Kcal/100 ml.

21. The composition of claim 16 wherein the protein material contains about 50% by caloric content of caseinoglycomacropeptides.

22. The composition of claim 21 including a source of carbohydrates, a source of lipids, and vitamins and minerals.

23. The composition of claim 16 wherein the composition is in the form of a pet food.

24. The composition of claim 23 in which the source of lipids represents up to 60% of the total energy and the quantity of proteins up to 40% on the basis of the dry extract.

25. A composition intended to be enterally administered to a mammal containing a slow-digesting protein material, the slow-digesting protein material having been previously treated so as to convert fast-digesting proteins which the slow-digesting protein material contained to slow-digesting proteins.

26. The composition of claim 25 wherein the slow-digesting protein material includes particulate gelled proteins combined with polysaccharides under conditions of thermodynamic incompatibility.

27. The composition of claim 25 wherein the polysaccharides are chosen from the group consisting of: alginates; xanthan gum; gum arabic; guar; starch; maltodextrin and dextrins; pectins; kappa-carrageenans; iota-carrageenans; lambda-carrageenans; methyl cellulose and carboxymethyl cellulose; sulfated dextrans; and gellan gum.

28. The composition of claim 25 comprising:
a source of proteins providing at least 8% of the total energy;
a source of carbohydrates providing up to 70% of the total energy; and
a source of lipids providing up to 35% of the total energy.

29. The composition of claim 25 having an energy density of between approximately 70 to about 200 Kcal/100 ml.

30. The composition of claim 25 wherein the slow-digesting protein material contains about 50% by caloric content of caseinoglycomacropeptides.

31. The composition of claim 30 including a source of carbohydrates, a source of lipids, and vitamins and minerals.

32. The composition of claim 25 wherein the composition is in the form of a pet food.

33. The composition of claim 32 in which the source of lipids represents up to 60% of the total energy and the quantity of proteins up to 40% on the basis of the dry extract.

* * * * *